United States Patent [19] [11] Patent Number: 4,555,274
Kitajima et al. [45] Date of Patent: Nov. 26, 1985

[54] ION SELECTIVE ELECTRODE AND PROCESS OF PREPARING THE SAME

[75] Inventors: Masao Kitajima; Osamu Seshimoto, both of Saitama; Shigemitsu Mizutani, Kanagawa, all of Japan

[73] Assignee: Fuji Photo Film Co., Ltd., Kanagawa, Japan

[21] Appl. No.: 618,285

[22] Filed: Jun. 7, 1984

Related U.S. Application Data

[62] Division of Ser. No. 475,672, Mar. 15, 1983, Pat. No. 4,528,085.

[30] Foreign Application Priority Data

Mar. 15, 1982 [JP] Japan ................................ 57-40398

[51] Int. Cl.⁴ .............................................. C25F 5/00
[52] U.S. Cl. .............................. 148/6.14 R; 427/124; 427/58; 148/6.2
[58] Field of Search ............................. 204/415–420; 148/6.3, 6.2, 6.14 R; 427/58, 124

[56] References Cited

U.S. PATENT DOCUMENTS 4,053,381 10/1977 Hamblen ............................ 204/418
4,273,639 6/1981 Gottermier ........................ 204/415
4,450,064 5/1984 Hamar ................................ 204/415

Primary Examiner—Sam Silverberg
Attorney, Agent, or Firm—Sughrue, Mion, Zinn, Macpeak, and Seas

[57] ABSTRACT

An ion selective electrode comprising a support having provided thereon, in sequence, a conductive layer and an ion selective layer, which is characterized by having at least one groove through the conductive layer and covering the surface of the groove with the ion selective layer is disclosed. Half cells or electrodes useful for the measurement of ionic activity of chlorine, sodium, potassium or, carbonate or hydrogen carbonate ions in blood or other aqueous sample liquids can be prepared in an extremely simple manner. The single ion selective electrode element comprising paired ion selective electrodes in accordance with the present invention are electrochemically equivalent. A process for forming the same is also disclosed.

22 Claims, 12 Drawing Figures

ION SELECTIVE ELECTRODE AND PROCESS OF PREPARING THE SAME

This is a division of application Ser. No. 475,672, filed Mar. 15, 1983, now U.S. Pat. No. 4,528,085.

FIELD OF THE INVENTION

The present invention relates to an electrode for measuring ionic concentration or ionic activity, more particularly to an ion selective electrode for potentiometrically measuring the ionic activity of body fluids such as blood, serum, other aqueous liquids, etc., and to an ion selective electrode assembly for measuring ionic activity using the ion selective electrode.

The present invention further relates to a device for measuring ionic activity.

BACKGROUND OF THE INVENTION

In general, the measurement of the concentration of inorganic ions such as $K^{\oplus}$, $Na^{\oplus}$, $Cl^{\ominus}$, $HCO_3^{\ominus}$ or $CO_3^{2\ominus}$, $Ca^{2\oplus}$, etc., in body fluids is important in the clinical field and wet procedures using ion selective electrodes have already been used in the art for this purpose for an extended time.

Known methods involving ion selective electrodes are of the type where ionic activity is measured by immersing a needle-like electrode in a liquid. It is troublesome to control such an electrode from the viewpoint of maintenance, washing, conditioning, life span, damage, etc., and it is necessary to use more than several hundred $\mu l$ of sample liquid since the electrode head must be sufficiently immersed in the sample liquid.

To eliminate such inconveniences, an electrode in a film or sheet form such that a sample liquid is spotted or dropped on a dry electrode in a film form is disclosed in Japanese Patent Application (OPI) No. 142584/77 (the term "OPI" as used herein refers to a patent application which has not yet been examined but is open to public inspection) and in U.S. Pat. No. 4,053,381. The film form ion selective electrode disclosed is a dry operative electrode formed by coating, on a metal layer, a layer of a water-insoluble salt of the same metal as in the metal layer, a dried electrolyte layer composed of a hydrophilic binder matrix containing dissolved therein a water-soluble salt having the same anion as that of the foregoing water-insoluble salt, and an ion selective layer on an insulating support film in this order. Two of these electrode films are connected together by a bridge to form a pair of electrodes. After connecting the electrodes to a potentiometer, a sample liquid and a reference liquid are dropped onto each of the electrodes, respectively, and the potential difference is measured, whereby the ionic activity of the sample liquid can be determined.

In these dry type ion selective electrodes, a specified ion can be measured by changing the kind of the ion selective membrane as the uppermost layer and hence there are many kinds of such electrodes, each to measure separate ion, e.g., $K^{\oplus}$, $Na^{\oplus}$, $Cl^{\ominus}$, $HCO_3^{\ominus}$ or $CO_3^{2\ominus}$, etc.

In the measurement of ionic activity, it is most important that a conductive layer of the ion selective electrode generate a potential response corresponding only to the ionic activity of a substance to be tested and not generate any other potential response.

A typical example involving an undesired potential response is the occurrence of an incorrect potential due to shorting. That is, when a sample liquid and a reference liquid are respectively dropped onto the foregoing electrode films, each drop of the sample liquid tends to spread over the surface of the ion selective layer (or a protective layer when a protective layer is formed on the ion selective layer) of each electrode film. The spread liquid flows down over the edge of the electrode film to short circuit various layers comprising the electrode, which results in the generation of an incorrect potential or zero potential to give an incorrect potentiometer value. Consequently, it is necessary in such ion selective electrode film to avoid such short circuiting by the sample liquid or reference liquid.

Japanese Patent Application (OPI) No. 142584/77 proposes a method of preventing the occurrence of short circuiting (hereafter often merely shorting) of the layers of an electrode film by forming a platform made of a plastic material or a strip made of a water-impermeable, electrically insulating adhesive for protecting the electrode edges in such a manner that only the ion selective layer of the electrode film is exposed and other portions of the electrode film are not permeated with or contacted by water or an aqueous liquid. However, such a procedure is labor intensive since each electrode must be so treated and it is difficult to completely avoid shorting since the processing requirements are exacting.

In U.S. Pat. No. 4,053,381 an ion selective electrode composed of three layers, i.e., a water-insoluble salt layer, an electrolyte layer and an ion selective layer, which is obtained by forming paired conductive layers with two pieces of conductive metals and forming the three layers thereon in common to the paired conductive metal layers, not forming these layers on each of the paired conductive metal layers, is disclosed. In a device for determining ionic activity as disclosed in this U.S. Patent, however, edges are inevitably formed and the device is constructed such that the disclosed film form electrodes in which edges of the electrode layers so exposed are fixed in a frame, i.e, a special frame for anti-shorting is used so that a dropped sample liquid as well as a reference liquid do not spread from the dropped area to an undesirable area (especially facing areas of two electrodes) to prevent both liquids from being brought into contact with each other to cause shorting or preventing both liquids itself from flowing down over the edge of the electrode film to short the layers of the electrode.

In order to obviate such shortcomings in the prior art, the present inventors found that when a conductive layer is covered with an ion selective layer, no particular anti-shorting means is required and a patent application directed to an invention based on this finding was filed (Ser. No. 397,705 filed July 13, 1982).

In addition to such anti-shorting means, it is important that a conductive layer of an ion selective electrode should not be in electrical contact with respect to a reference electrode. In order to avoid such electrical contact, particularly in the case of a differential method in which paired electrodes are employed, the distance between the electrodes is maintained as great as possible so that the possibility of electrical contact is lost and insulation is assured. In such case, however, the time period until a potential difference generates by diffusing both sample and reference liquids into a bridge, forming an interface between the liquids and thus achieving electrical conduction, is prolonged and rapid measurement is not possible. On the other hand, it is necessary that an ion selective electrode be as small as possible, particularly in case where paired electrode films are employed as a differential electrode or in the case where multiple ions are to be examined at the same time, it is desired that each ion selective electrode be as close as possible. Such, however, increases the danger of electrical contact between a conductive layer of one ion selective electrode and a conductive layer of another ion selective electrode, since ion selective electrodes that should avoid an incorrect response other than a potential response based on ionic activity of a substance to be tested. It has thus generally been thought impossible to realize such a demand in the prior art.

One exception is an embodiment described in U.S. Pat. No. 4,053,381 in which all necessary layers are formed on a support to yield a single element on the common support, after which electrical separation of a metal layer thereof is achieved by skiving a groove through the metal layer so that the electrode can be used for potential measurement as a paired electrode. In this case, the metal layer is electrically separated only by the skived groove and, accordingly, such construction is advantageous from the viewpoint of reducing the size of the ion selective electrode. However, after all of the operative layers of the ion selective electrode are formed the skiving of the groove is conducted so that the operative layers of the electrode, including the metal layer in question, possess edges exposed at the skived portion. As has been discussed above, there is then the problem that the exposed metal layer would short due to liquid drops flowing over the edges to thereby cause an incorrect potential. Therefore, it is necessary per such U.S. patent that complicated anti-shorting means be provided as described above. In this U.S. patent mention is made of continuous half cell electrode-construction layers (three layers: an ion selective layer, an electrolyte layer and a layer of a water-insoluble salt of the metal) other than a support and metal layers formed as continuous layers, respectively, but only the metal layers are separated to achieve electrical insulation. However, this construction is the same as other electrodes in that edges of the metal layers are exposed also in such a half cell and special anti-shorting must be provided.

SUMMARY OF THE INVENTION

Therefore, one object of the present invention is to provide a dry type ion selective electrode which eliminates the aforesaid anti-shorting problems encountered in the prior art.

A further object of the present invention is to provide an ion selective electrode which enables accurate potential response without need of any complicated anti-shorting design.

Another object of the present invention is to provide a process of preparing a new type of ion selective electrode in an extremely simple manner at low cost.

A further object of the present invention is to provide an ion selective electrode assembly, i.e., a single electrode element comprising a paired ion selective electrodes capable of construction on a very compact size.

The ion selective electrode in accordance with the present invention comprises a support having formed thereon, in sequence, a conductive layer and an ion selective layer, and is characterized in that:

(1) the conductive layer possesses at least one groove; and;

(2) the surface of the groove is covered with the ion selective layer.

In the figures, the numerals mean:
110: groove
11: conductive layer
111: silver layer
12: water-insoluble metal salt layer
121: silver halide (or chloride) layer
14: ion selective layer
19: support
52: electrical connection terminal for potential measuring apparatus
S: sample liquid
R: reference liquid

DESCRIPTION OF THE PREFERRED EMBODIMENTS

Figure 1:
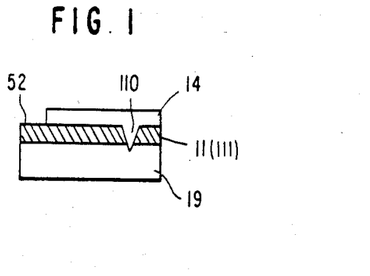
FIG. 1 is a cross-sectional view showing the basic structure of an ion selective electrode in accordance with the present invention.
Figure 2:
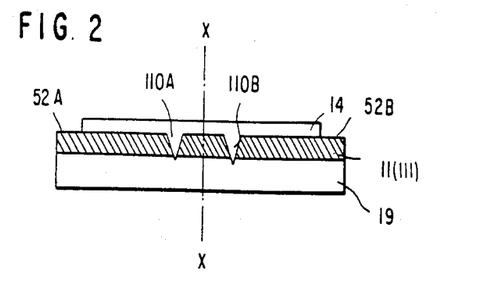
FIG. 2 is an outlined cross-sectional view representing the case in which the ion selective electrode is cut along line X—X to form two ion selective electrodes as shown in FIG. 1.

The term "electrode" as used herein also includes a half cell or single electrode as illustrated in FIGS. 1 and 2.

In the present invention, a first characteristic feature resides in that insulation of the conductive layer is achieved by providing a groove. The groove is provided to electrically insulate the conductive layer and therefore any shape is acceptable so long as such purpose is accomplished. However, the groove is most typically provided by marking-off, scratching or skiving as will be later described so that the groove usually takes a V-shape (numeral 110) as shown in FIG. 1.

When a groove is skived in the conductive layer which was initially a single continuous layer, the resulting conductive layers are separated from each other by the thus formed groove but at least one part of the conductive layer must have an area sufficient for assuring an electro-motive force (potential) when a sample liquid or a reference liquid is applied to the ion selective layer of the ion selective electrode. It is desired that this area be provided at the site at which the electrical connection terminal is provided when part of the conductive layer is exposed since this area should function as an electrical terminal for connecting a potential measuring apparatus.

A second characteristic feature of the present invention resides in the fact that exposed edges resulting from the skiving operation forming the groove are not formed because forming the groove is effected after the conductive layer is provided on the support but before the ion selective layer is provided thereon, subsequently covering the groove with the ion selective layer.

The characteristic features of the present invention will be described in more detail with reference to the drawings. In the drawings, numerals 11 and 111 are interchangeably used to mean a conductive layer and a silver layer as a specific example of the conductive layer, respectively; numerals 12 and 121 are also interchangeably used to refer to a water-insoluble metal salt layer (12) and a silver halide (or chloride) layer (121) as a specific example of the water-insoluble metal salt layer.

FIG. 1 represents the most basic layer structure of the ion selective electrode in accordance with the present invention. Electrically conductive layer 11 is located on support 19 and possesses a groove shown by numeral 110. The groove 110 can be formed by any desired procedure for forming a groove, e.g., marking off or scratching the surface of the conductive layer 11 with a sharp knife, etc., after the conductive layer 11 is provided on the support 19 but before the ion selective layer 14 located thereon is provided. Groove 110 is formed primarily to provide an electrically insulating area in the conductive layer 11. Accordingly, it is sufficient that conductive layer 11 is merely separated by groove 110; however, in order to ensure insulation, it is preferred that the groove reach support 19. Taking it into account that the conductive layer is extremely thin, forming a groove in the conductive layer alone would require very precise operation and such groove formation is rather difficult.

From the viewpoints that the conductive layer is extremely thin as described above and the ion selective layer is subsequently coated thereon to render insulation complete, it is preferred that the depth of the groove should be deep to such extent that the support is not substantially damaged; in other words, to such extent that the support is not cut out or divided into two portions. The depth of the groove varies depending upon layer thickness and the materials of the support and metal layer, etc., and cannot be determined by a specific numerical value but is generally 10 times or more the thickness of the conductive layer, i.e., about 2 or 3 $\mu$m or more. The maximum depth of the groove is functionally up to a depth in which the support is neither damaged nor divided into two portions. A thin support thus provides the shallow maximum depth and a thick support provides rather the deep maximum depth. Taking it into account that the support should maintain its plane surface, however, it is practical that the maximum depth of the groove be set forth to about $\frac{1}{2}$ of the thickness of the support. Taking a support having a thickness of 185 $\mu$m as an example, the maximum depth is generally about 120 $\mu$m, preferably 100 $\mu$m. Thus when the layer thickness of the conductive layer 11 is, for example, 500 nm and the layer thickness of the support 19 is 185 $\mu$m, it is most preferred that the depth of the groove be in the range of about 5 to about 120 $\mu$m, particularly 10 to 100 $\mu$m. The width of the groove opening (opening width) can be narrow as possible so long as insulation of the conductive layer is realized; considering possible conduction during subsequent measurement, however, it is preferred that the opening width be about 10 $\mu$m to about 1 mm, particularly 50 $\mu$m to 300 $\mu$m.

The location of the groove is determined by the shape of the ion selective electrode (e.g., a half cell or an electrode suited for a differential method, etc.), etc., in addition to the intended insulating function, as will later be described. However, the groove should at least be located at an area which insures an area generating an electro-motive force (potential) when one of the divided ion selective electrode is brought into contact with a sample liquid. An exposed area (which is shown by numeral 52) of the conductive layer which functions as a terminal for electrical connection is provided at the side in which such a surface area is ensured. If electrical contact with the conductive layer is achieved by means of piercing a needle-like probe, etc., therethrough, there is, of course, no need to expose area of the conductive layer, and the groove can optionally be located by any desired place.

After the conductive layer 11 is separated from each other by the groove 110, the ion selective layer 14 is coated thereon. Ion selective layer 14 covers conductive layer 11 at portions other than the terminal area shown by numeral 52 and, at the same time, groove 110 is covered with the ion selective layer 14, i.e., the conductive layers 11 which are physically separated from each other by groove 110 to achieve electrical insulation are further covered with the electrically insulating ion selective layer 14 to thereby enhance insulation. It is sufficient for achieving the electrical insulation that the resistivity of ion selective layer 14 be at least about $10^4$ ohm.cm, preferably in the range of from $10^5$ to $10^{10}$ ohm.cm, more preferably $10^6$ to $10^{10}$ ohm.cm.

Further, at an area where the occurrence of shorting is most likely to occur among the areas functioning as the ion selective electrode and a bridge is thus set, the conductive layer 11 has no exposed edge due to covering the groove 110 with the ion selective layer 14. Thus, even if a sample liquid or a reference liquid were to spread over the right edge or face to FIG. 1 and to flow down to the conductive layer 11, the area of the ion selective electrode which functions so as to generate a potential is insulated by the groove 110. Therefore, there is no possibility of shorting in the ion selective electrode of the present invention.

It is preferred that the ion selective layer be formed such that substantially all of the exposed surfaces including the internal surface of the groove, the bottom surface of the groove formed in the support, etc. be covered. By covering substantially all of the surfaces with the ion selective layer, insulation between the two conductive layers separated from each other by the groove becomes more complete because both the ion selective layer and the protective layer are per se substantially electrically insulative in a dry state. However, it is often sufficient that the covering is made so as to realize insulation merely to an extent that no problem is encountered in potential measurement.

The ion selective electrode (half cell) shown in FIG. 1 can also be prepared by forming grooves symmetrically at two portions 110A and 110B as shown in FIG. 2, coating the grooves and the portion converted into silver chloride with an ion selective layer 14 and then cutting along line X—X. According to this procedure, two half cells can be prepared at the same time merely by forming two grooves. This procedure is advantageous not only simplifying procedural steps but also in obtaining electrochemically equivalent half cells. In the measurement of ionic activity, a measurement method for reading a potential using a pair of electrodes (differential method) is very practical and has thus been widely employed; in this case, it is ideal that both electrodes have the same electrochemical properties. However, electrodes are usually prepared independently, e.g., by a procedure in which a long film is cut into electrodes, and the electrodes are mounted in a plastic frame, etc., as a pair for actual use. As a matter of course, it is almost impossible that the thus independently prepared two electrodes would possess the same physical and electrochemical properties. However, according to the foregoing procedure, equivalent electrodes can be obtained simultaneously in an extremely simple manner.

Figure 3A:
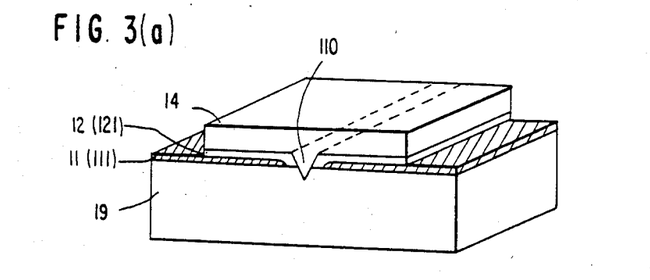
FIG. 3(a) is a perspective view of a preferred embodiment of a single electrode element comprising a paired ion selective electrode in accordance with the present invention which is employed as a differential method and FIG. 3(b) is an enlarged cross-sectional view of such an electrode element.
Figure 3B:
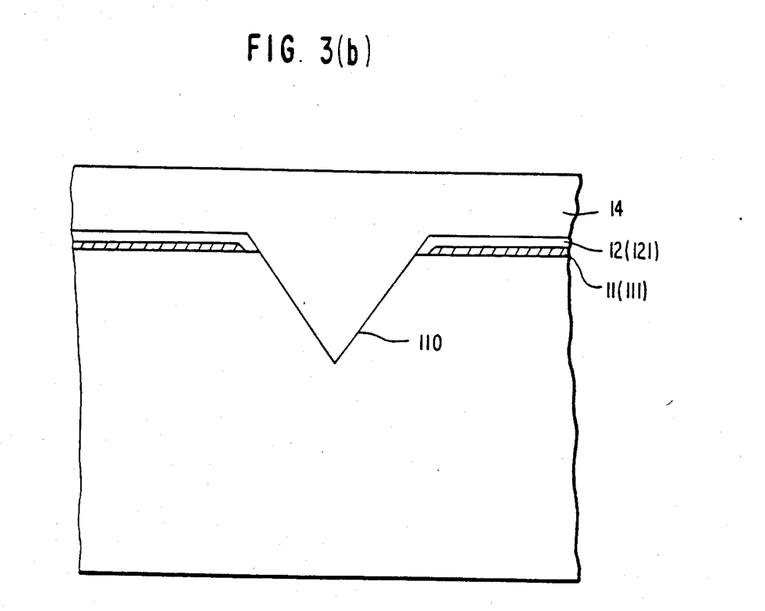

In FIG. 3, which illustrates a single electrode element comprising such procedure, a paired ion selective electrode in which a conductive metal layer 11 (111) is symmetrically separated by a groove 110 on a common support 19 (to realize insulation) is then covered with a water-insoluble metal salt layer 12 (121) and an ion selective layer 14. The thus obtained ion selective electrodes have an appearance as if they were a half cell; however, perfect insulation is achieved by the groove 110 and further by the covering with the metal salt layer 12 (121) and the ion selective layer 14, having high electrical resistance, a single electrode element comprising a paired electrode for differential method is thus formed where, electrochemical equivalency is perfect since the respective constructing operative layers are provided on the common support under the same conditions in the same manner and their function as two electrodes is realized simply by scratching to form the groove 110.

The electrode shown in FIG. 3 is formed by firstly providing a conductive metal (silver) layer 11 (111) on the common support 19 by means of deposition, plating, or the like, then scratching the metal layer 11 (111) at the surface thereof to form groove 110, then oxidative-halogenating to form a silver halide layer 12 (121), and then covering the entire surface of the metal layer 11 (111) and groove 110 with ion selective layer 14. The ends of the silver layer 11 (111) are in part exposed as electrical terminals by masking the portions for the terminal area at the step of oxidative-halogenation in a conventional manner. Details of oxidative-halogenation are described in, e.g., U.S. Pat. No. 4,053,381, which is hereby incorporated by reference.

Per the present invention, perfect insulation is attained, as described above, by physical separation with a groove(s) and the covering thereof with an ion selective layer. In this case, it has been found unexpectedly that when oxidative-halogenation was conducted according to the embodiment shown in FIG. 3, the cross section (width W in FIG. 3 (b)) of groove 110 previously formed was unexpectedly enlarged. It has also been found that any metal silver scraps remained at groove 110 resulting from the formation of groove 110 were removed during the step of oxidative-halogenation. This is believed to be due to the fact that oxidative-halogenation is initiated at the surface and gradually goes down into the interior thereof. Further, the silver halide layer 12 (121) is formed so as to cover the edges of the silver layer 11 (111) corresponding to the cut end of the groove 110, as shown in FIG. 3 (b) in an enlarged view.

The ion selective layer 14 which is electrically insulating in a dry state is further coated thereon. Accordingly, not only does electrical insulation becomes perfect but also such a construction prevents short circuiting at the same time.

Insulation between the conductive layers is sufficiently achieved if these layers are separated by a single groove. However, in order to be more complete, two or more grooves can be provided. In addition to insulation between the conductive layers, which is most important in terms of preventing conduction, one or more grooves can also be formed at another edge from which a liquid spread over a side opposite an ionic flow (i.e., outerwards and finally over the edge to the thickness direction) might be sometimes flown down to the thickness direction at the edge to thereby cause short circuiting. A representative example is shown in FIGS. 4, 7 and 9.

Figure 4:
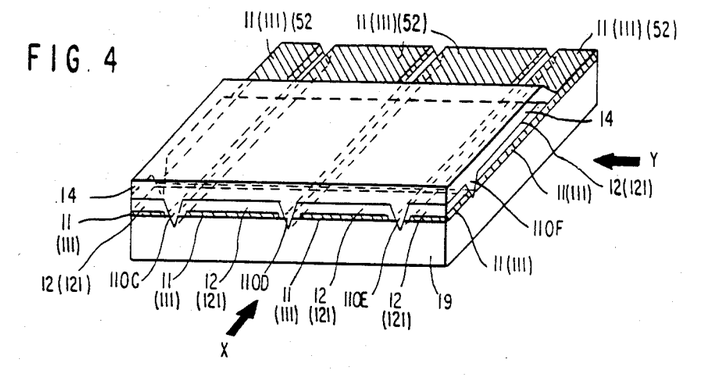
FIG. 4 is a perspective view showing another preferred embodiment of a single electrode element comprising a paired ion selective electrode according to the present invention.
Figure 5:
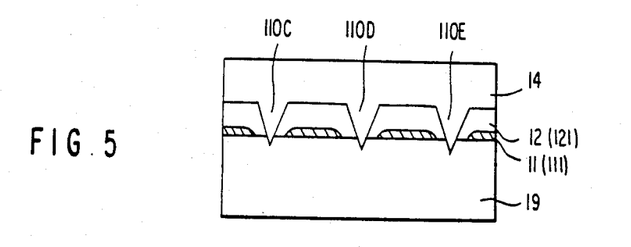
FIGS. 5 and 6 are cross-sectional views of an ion selective electrode shown in FIG. 4 when viewed from arrows X and Y, respectively.
Figure 6:
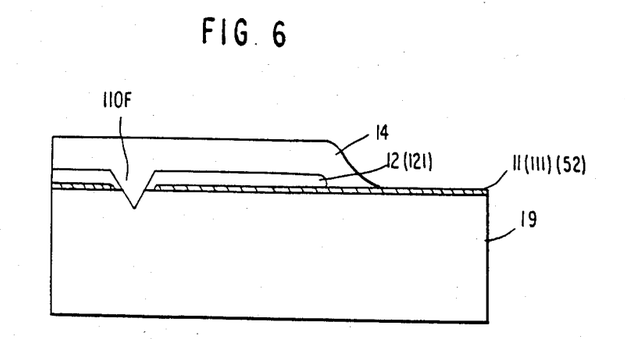

FIG. 5 and FIG. 6 each represents a cross sectional view of a single electrode element comprising a paired ion selective electrode involving a plurality of grooves as shown in FIG. 4 when viewed from arrows X and Y, respectively. As will be understood from these figures, the conductive layers 11 which are separated from one another have no exposed portion at any edge. Therefore, an ion selective electrode in accordance with the present invention functions as a paired electrode for a differential method while its appearance is seemingly a half cell and the same eliminates any chances of short circuiting. The ion selective electrode of the present invention which has such a construction does not require any anti-shorting means as required in the prior art.

Figure 7:
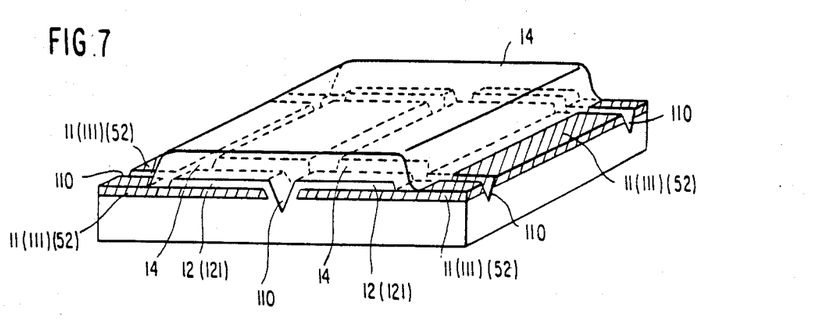
FIG. 7 is a perspective view showing another preferred embodiment of a single electrode element comprising a paired ion selective electrode according to the present invention and FIG. 8 is a plane view of a paired ion selective electrode shown in FIG. 7.
Figure 8:
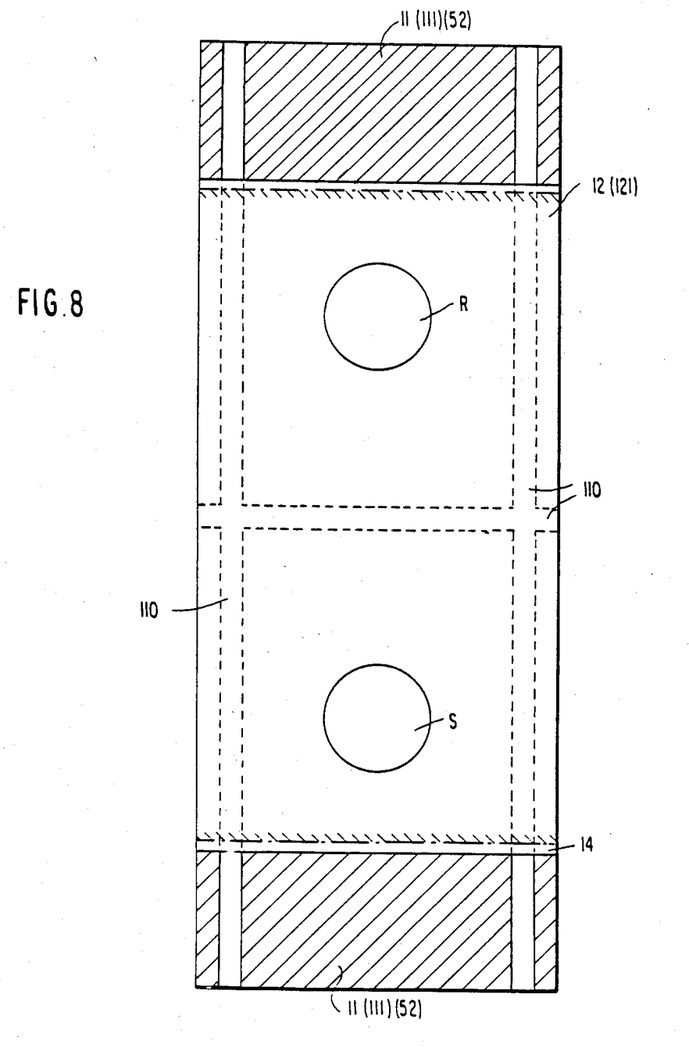

FIG. 7 represents a perspective view showing a single electrode element comprising a paired ion selective electrode wherein three grooves are provided and electrical insulation is completely achieved. FIG. 8 is a plane view of the single electrode shown in FIG. 7. This electrode has no exposed edges at areas where the occurrence of shorting is most likely to occur. The electrode having the construction as shown in FIGS. 7 and 8 is preferred since electrical terminals are located at the farthest edges of the paired electrode.

Figures 9, 10:
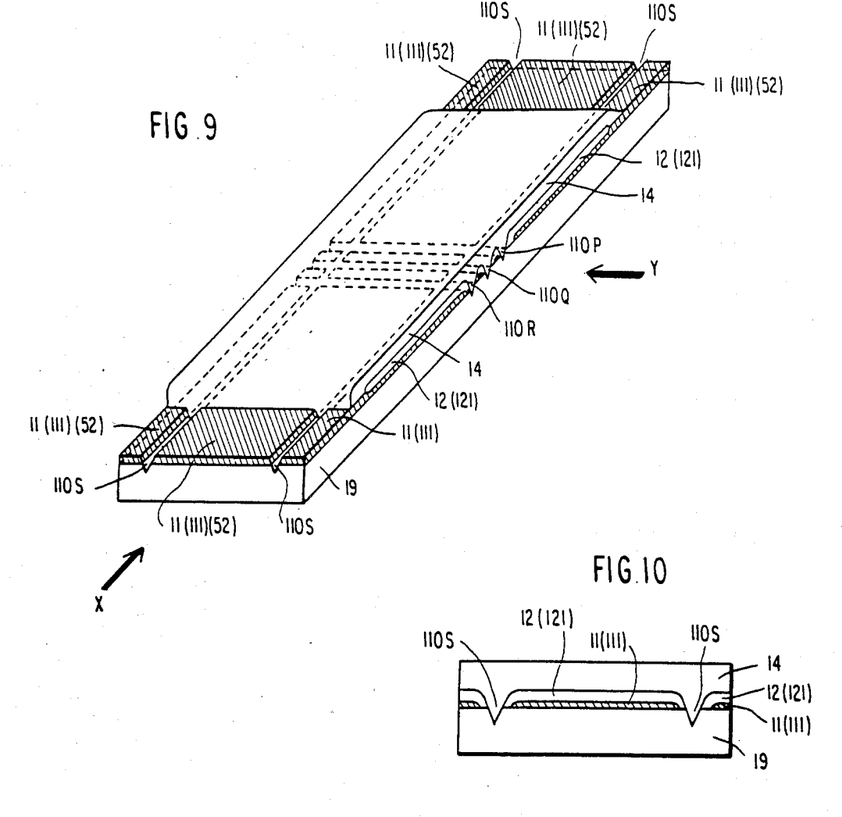
FIG. 9 is a perspective view showing another preferred embodiment of a single electrode element comprising a paired ion selective electrode according to the present invention.
FIGS. 10 and 11 are cross-sectional views of a paired ion selective electrode shown in FIG. 9 when viewed from arrows X and Y, respectively.

FIG. 9 is a perspective view of a single electrode element comprising a paired ion selective electrode having three grooves 110Q, 110P and 110R for separating conductive layer 11 (52) from one another, and grooves 110S for rendering electrical insulation perfect at edges in the width direction. This construction of the electrode is particularly preferred since undesired contact of a sample liquid and/or a reference liquid with conductive layer 11 (52) is doubly prevented by groove 110Q.

Again, the characteristic feature of the present invention resides in skiving a groove(s) in a continuous layer comprising a support having provided thereon a metal layer, thereby electrical conduction being prevented, then oxidative-halogenating the same and, covering with an ion selective layer. The thus obtained electrode requires no anti-shorting means and functions as a paired electrode suited for a differential method. In the prior art, a paired electrode was prepared by placing two electrodes independently prepared in juxtaposition. In the prior art method represented by U.S. Pat. No. 4,053,381, all of electrode layers were formed through continuous operations followed by cutting into half cells. Accordingly, facing edges of two half cells are necessarily exposed and such exposed edges facing each other (which correspond to exposed sides in the thickness direction in U.S. Pat. No. 4,053,381) are most likely to occur shorting which gives incorrect reading of a potentiometer. For this reason, it is inevitable to provide an anti-shorting means in the prior art electrode. However, no anti-shorting problem is involved in the electrode of the present invention because such facing edges are fully covered with an ion selective layer.

As materials for constructing the dry type ion selective electrodes in accordance with the present invention, materials used for known electrodes in this art can be used.

First, as the conductive metal for the ion selective electrodes of the present invention, the conductive metals used for known electrodes disclosed in U.S. Pat. Nos. 4,053,381, 4,115,209 and 3,856,649 can be used. Preferred examples of the conductive metals used in the present invention are silver, platinum, palladium, gold, nickel, copper, aluminum, indium, etc.

Conductive metal oxides are also useful in the present invention to form the conductive layer; such are described in, for example, Per Kofstad, *Nonstoichiometry, Diffusion and Electrical Conductivity in Binary Metal Oxides*, New York, Woley Interscience (1972), etc. Practical examples of such conductive metal oxides are tin oxide ($SnO_2$), indium oxide ($In_2O_3$), zinc oxide (ZnO), iridium oxide ($IrO_2$), cadmium oxide (CdO), thallium oxide ($Tl_2O_3$), iron oxide ($Fe_3O_4$), lead oxide ($PbO_2$ or PbO), vanadium oxide ($V_2O_3$ or VO), bismuth oxide ($Bi_2O_3$), beryllium oxide (BeO), manganese oxide ($MnO_2$), molybdenum oxide ($MoO_2$), a mixture of tin oxide and antimony oxide, and a mixture of tin oxide and indium oxide. Preferred examples of the conductive metal oxides are tin oxide, indium oxide, zinc oxide, a mixture of tin oxide and antimony oxide, and a mixture of tin oxide and indium oxide.

Known methods can be utilized for formation of a thin conductive layer including a metal layer and a metal oxide layer. Representative examples of such known methods which are applicable to the formation of conductive layers include a vacuum deposition method, an electro-plating method and a chemical plating. In the case that silver is used as a metal, specific known methods are applied to the formation of a silver layer and examples of such include a method which comprises applying silver by vacuum deposition, a method which comprises carrying out chemical plating, a method which comprises providing a photographic silver halide-aqueous protective colloid emulsion layer and carrying out exposure-development to form, e.g., a metal silver layer, and a method which comprises dispersing conductive metal powders or conductive metal oxide powders in a binder to provide a conductive metal or metal oxide layer on a support and then drying the layer by evaporating solvent off, or solidifying the binder by polymerization or polymerization condensation to provide a conductive metal layer or a conductive metal oxide layer.

In the case of using binders, it is preferred that the same binders as those used for the ion selective layer which will be formed later or hydrophobic binders similar thereto be employed.

Known binders and solvents e.g., binders for the aforesaid dry-type electrodes can be employed. In addition thereto, binders freely chosen from binders for paints and adhesives can also be employed. Examples of binders include gelatin, polyacrylamide, polyvinyl alcohol, alcohol-soluble polyamide, cellulose diacetate, cellulose triacetate, polyvinyl pyrrolidone, chlorinated polyethylene, chlorinated polypropylene, polystyrene, etc.

These conductive layers are formed on the support and, in order to prepare them in a large scale, it is advantageous that the layers be formed on a support in a stripe or in a pattern, depending upon purpose and utility, in a manner as described in Japanese Patent Application (OPI) No. 10645/83 and Ser. No. 397,705 filed July 13, 1982.

The conductive metal can be used in foil- or film-form or thin layer-form on the support.

A conductive metal oxide which is self-supporting and has high mechanical strength may be used in the same form as a conductive metal as described above but a conductive metal oxide which is not self-supporting and has weak mechanical strength may be used as a thin metal oxide layer formed on a support such as glass, a ceramic, a polymer, paper, etc., which is coated with a thin layer of the metal oxide.

It is preferred that a thickness of a conductive layer, be it metal or metal oxide, generally be in the range of from about 50 nm to about 50 $\mu$m.

Supports employed for the ion selective electrode of the present invention can be widely chosen from known materials without any particular limitation as long as they can support other portions of the electrode, either be composed of materials electrically insulating and electrically inert. Preferred examples for the support include cellulose acetate, polyethylene terephthalate, polycarbonates such as polycarbonate of bisphenol A, polystyrene, etc. It is preferred that the support be formed generally have a thickness of from about 0.05 mm to about 0.5 mm.

A layer of a water-insoluble salt, which is formed on the conductive metal, can be formed by any known method. That is, for example, the layer may be formed by vacuum-deposition of a metal salt, etc.

When a metal layer is a silver layer, the layer can be formed by treating a silver layer with an aqueous $K_2Cr_2O_7$.HX solution or an aqueous $K_3[Fe(CN)_6]$NaOH-HX solution (in which X represents a halogen atom, e.g., chlorine, bromine, iodine). Of these, treating silver with a $K_2Cr_2O_7$-HCl solution is most excellent in view of stability.

When a silver layer is converted into silver halide through oxidative-halogenation, the width of the groove formed by skiving or scratching is enlarged to an opening width almost twice its initial width. Further, scraps which might be formed upon marking off or scratching are eliminated during the step of the oxidative-halogenation so that a smooth treated surface is obtained. This is believed to be because the oxidative-halogenation proceeds from the surface to the inside of the layer and scraps are trapped one by one into the silver halide layer formed as the oxidative-halogenation treatment proceeds to become a part of the continuous layer.

The thickness of the layer of the insoluble salt is generally 50 nm to 10 $\mu$m, preferably 50 nm to 1 $\mu$m.

In the case that the conductive metal layer is a silver layer, a part of the silver layer is exposed to function as a terminal for electric connection. In order to function as a terminal, one can mask the desired area by coating the portion with a resist, e.g., masking the portion by coating a resist which can be removed by alkali as disclosed in *Research Disclosure*, No. 19445, June 1980, masking the portion by forming thereon a thin vapor deposited layer of nickel or chromium having a thickness of 5 nm to 20 nm as disclosed in Japanese Patent Application (OPI) No. 33537/81 (corresponding to U.S. Pat. No. 4,259,164), masking the portion by forming thereon a thin vapor deposited layer of palladium having a thickness of 1.5 nm to 15 nm or a thin vapor deposited layer of indium having a thickness of 3 nm to 20 nm, or masking the portion using a Furon Mask (tradename, made by Furuto Sangyo Co., Ltd.). etc.

An electrolyte layer, which is formed, if necessary or desired, on the layer of a water-insoluble salt, may also be formed by any known method. For forming the electrolyte layer, the techniques described in Japanese Patent Application (OPI) No. 142584/77 (corresponding to U.S. Pat. Nos. 4,053,381, 4,11,246 and 4,214,968) and Japanese Patent Application No. 92379/80 (corresponding to Japanese Patent Application (OPI) No. 17852/82) can be employed.

The ion selective layer is a layer which has a selective response to a predetermined specific ion and is, preferably, electrically insulating in the dry state prior to being brought into contact with a sample liquid or a reference liquid. The term "selective response to a predetermined specific ion" includes not only the case of selectively permeating a specific ion only or responding to a specific ion only but also the case where a specific ion can be selected from other undesired materials with a sufficient time difference for the measurement. Further, the case where a potentiometric response corresponding to the change of ionic activity in a liquid is measured by ion exchange, whereby the same function as the function of selective response to a predetermined specific ion is obtained, is included in the term "selective response to a predetermined specific ion" in the present invention.

Since the sample liquid and the reference liquid are both aqueous liquids, the ion selective layer of the ion selective electrode of the present invention must be water-insoluble. The ion selective layer may be hydrophilic or hydrophobic if it is insoluble in water, but it is preferred that the ion selective layer be hydrophobic.

A most typical ion selective layer is composed of an ion carrier, an ion carrier solvent, and an organic hydrophobic binder (or a matrix of a hydrophobic organic binder).

As the ion carrier, there can be valinomycin, cyclic polyethers, tetralactone, macrolide actins, enniatins, monensin, gramicidins, nonactin, tetraphenyl borate, cyclic polypeptides, etc. Details are described in *Research Disclosure*, No. 16113, page 32, September (1977).

As the ion carrier solvent, there can be bromophenyl phenyl ether, 3-methoxyphenyl phenyl ether, 4-methoxyphenyl phenyl ether, dimethyl phthalate, dibutyl phthalate, dioctyl phthalate, dioctylphenyl phosphate, bis(2-ethylhexyl) phthalate, octyldiphenyl phosphate, tritolyl phosphate, dibutyl sebacate, etc. Details are described in *Research Disclosure*, No. 16113, page 33, September (1977).

As the hydrophobic organic binder, there can be hydrophobic natural or synthetic film-forming polymers such as, for example, cellulose esters, polyvinyl chloride, polyvinylidene chloride, polyacrylonitrile, polyurethanes, polycarbonates, vinyl chloride-vinyl acetate copolymers, etc.

As the ion carriers, ion carrier solvents, hydrophobic organic binders, and ion selective layers composed of these materials, the materials and techniques described in Japanese Patent Application (OPI) No. 142584/77, U.S. Pat. Nos. 4,053,381, 4,171,246 and 4,214,968, and *Research Disclosure*, No. 16113, September 1977 can also be used.

Ion exchange resins can also be used as material for the ion selective layer. In the case of using an ion exchange resin, a potentiometric response due to the change of ions in an ion-containing solution is measured.

The ion exchange resin used in the present invention may be cationic or anionic. Details of ion exchange resins and the formation of ion selective layers using them are described in Japanese Patent Publication No. 47717/77 (corresponding to U.S. Pat. No. 4,115,209).

An ion selective layer is required when the ion to be measured is $K^\oplus$, $Na^\oplus$, $Ca^{2\oplus}$, or $HCO_3^\ominus$ or $CO_3^{2\ominus}$, but the ion selective layer is unnecessary when the ion to be measured is $Cl^\ominus$, the electrode is a metal layer composed of silver, and the layer of the water-insoluble metal salt is composed of silver chloride. In the latter case, in place of the ion selective layer, a layer composed of a material as described in Japanese Patent Application (OPI) No. 89741/80 (corresponding to U.S. Pat. Nos. 4,199,411 and 4,199,412), such as cellulose esters (e.g., cellulose acetate butyrate, cellulose acetate propionate, hydrolyzed cellulose acetate butyrate, and mixed esters thereof) or a latex as described in Japanese Patent Applications (OPI) No. 72622/78 and 1384/79 is formed as a protective layer having permeability for the ion being detected.

The ion selective layer, which is formed on the conductive metal layer or conductive metal oxide layer, can be formed by any known method. For example, an ion carrier can be dissolved in a solvent and, after adding the solution to a binder solution, the mixture coated and dried. The concentration of the ion carrier is generally about 0.05 g/m$^2$ to about 10 g/m$^2$ and the thickness of the ion selective layer is about 3 µm to about 125 µm, preferably about 5 µm to about 50 µm.

For measuring ionic activity using the ion selective electrode of the present invention, a sample liquid and a reference liquid are dropped onto each electrode (more specifically, an ion selective layer or a protective layer) at the same time, which electrodes are separated from each other by a groove and connected by a bridge for generating and promoting electrical conduction due to ionic flow between the liquid-liquid required for the potential measurement, thereby generating a potential difference in response to ionic activity, and the potential change is read by a potentiometer.

Known meaterials for bridges can be utilized. Examples for the material for a bridge include porous materials such as porous paper (filter paper, blotting paper), membrane filter, cotton materials (cotton cloth), etc. Preferred examples of bridges are shown in Japanese Patent Applications (OPI) 142584/77 (corresponding to U.S. Pat. Nos. 4,053,381, 4,214,968 and 4,171,246), 59326/80, 71924/80, 20499/80 (corresponding to U.S. Pat. No. 4,148,936), Japanese Utility Model Application (OPI) 64759/80, etc.

The present invention will now be described in more detail with reference to the following examples.

EXAMPLE 1

Onto a polyethylene terephthalate (PET) film having a thickness of 180 µm, silver was deposited in a thickness of about 800 nm. The film was cut into pieces 32 mm wide and 10 m long. A scratched groove was then formed through the silver layer at the center of the film surface with a cutter (NT Cutter Model A-300, manufactured by Nippon Tensha-shi (K.K) along the center line thereof in the length direction without cutting the PET film in two. Electrical insulation test using a tester showed perfect insulation. The groove dept was 100 μm and the opening width was 70 μm.

A conventional liquid masking agent was then coated on portions (to be masked from subsequent oxidative-chlorination, 10 m long and 5 mm wide from the respective edges in the 32 mm width direction) of the silver-deposited PET film in the length direction thereof followed by drying. The film was then treated (treatment for oxidative-chlorination) was an aqueous solution composed of 5 g. of hydrochloric acid (36%), 7 g. of potassium bichromate and 1 liter of water at 35° C. for 60 seconds to convert the surface of the silver layer into a silver chloride layer. Thereafter, the film was washed with water and then dried. Microscopic observation indicated a broadening of the groove width to about 100 μm after the chlorination and electrical insulation was further improved.

EXAMPLE 2

The scratched groove of the silver surface per Example 1 could be carried out continuously by running a PET film at constant speed as shown below.

While running a silver-deposited PET film (32 mm wide and 2 m long) obtained in a manner similar to Example 1 to the length direction of the silver-deposited film at a 6 m/minute speed, a scratched groove was formed by putting a cutter knife on the film to a depth where electrical insulation was attained. The depth of the resulting cut end was about 50 μm.

A film-form Ag/AgCl electrode having a scratched groove was obtained through oxidative-chlorination similar to Example 1, and electrical insulation test using a tester indicated that perfect insulation was achieved.

Example 3

A film-form Ag/AgCl electrode having a scratched groove was obtained in a manner similar to Example 2 except that after the oxidative-chlorination the silver chloride layer was scratched by putting a cutter knife on the silver chloride layer. Also in the case that scratching was carried out after the chlorination, a completely electrically insulating electrode was obtained as in Example 2. The groove had a depth of 100 μm and a width of 100 μm.

In Examples 1 through 3, only one scratched groove was formed, but the number of scratched groove could be increased to 2 or 3 (double or triple scratched grooves), if necessary or desired. It was found that electrical insulation was also perfect when the number of the scratched groove was increased.

EXAMPLE 4

An acetone solution containing 10 wt% of cellulose acetate (degree of acetylation, 39.4%, manufactured by Eastman Chemicals Co., Ltd.) and 5 wt% of polyethylene glycol (average molecular weight 400) was coated over substantially the entire surfaces of the AgCl layer and the scratch-grooved portion of the Ag/AgCl electrode obtained in Example 2 to provide a protective layer having a dry thickness of 3 μm thereon.

Microscopic observation of the vicinity of the scratch-grooved portion indicated that the scratch-grooved portion was of the shape shown in the cross sectional view of FIG. 3.

The thus obtained long electrode was cut into a size of about 6 mm. Using a paper bridge (Japanese Patent Application (OPI) 14050/83), potential generated by $Cl^{\ominus}$ activity in the sample liquid was measured using Olion Microprocessor Ion Analyzer Model 901.

The results are shown in Table 1, in which VERSATOL (tradename, manufactured by General Diagnostic Co., Ltd., hereafter the same) was employed as a reference liquid and the potential value is an average of 11 measurements.

TABLE 1

| $Cl^{\ominus}$ Ion Activity | 77 meq/l | 102 meq/l | 120 meq/l |
|---|---|---|---|
| Potential (mV) | 5.7 | −0.26 | −4.1 |
| σ | 0.30 | 0.26 | 0.1 | n = 11
σ: standard error (hereafter the same)

As shown in Table 1, a good linear relationship was obtained between the logarithm of $Cl^{\ominus}$ activity and potential with good reproducibility.

EXAMPLE 5

A protective layer having a dry thickness of 5 μm was formed on the electrode of Example 2 in a manner similar to Example 4 except that a latex (styrene-butyl acrylate-acrylic acid-hydroxymethylacrylamide: 50-42-2-6% by weight) described in Japanese Patent Application (OPI) No. 92887/81 was employed. Evaluation for $Cl^{\ominus}$ activity was carried out as in Example 4.

The results obtained are shown in Table 2.

TABLE 2

| $Cl^{\ominus}$ Ion Activity | 77 meq/l | 102 meq/l | 120 meq/l |
|---|---|---|---|
| Potential (mV) | 6.0 | −0.3 | −3.9 |
| σ | 0.60 | 0.5 | 0.3 |

As is clear from Table 2, a good linear relationship was obtained between the logarithm of $Cl^{\ominus}$ activity and potential with good reproducibility.

EXAMPLE 6

A $K^{\oplus}$ ion selective electrode was prepared in a manner similar to Example 2 except that a solution for an ion selective layer comprising:

| | |
|---|---|
| Vinyl chloride-vinyl acetate copolymer "VYNS" (polymerization ratio = 90:10, manufactured by Union Carbide Co., Ltd., hereafter the same) | 0.9 g |
| Dioctyl phthalate | 2.4 g |
| Valinomycin | 0.044 g |
| Methyl ethyl ketone (MEK) | 5 g | was coated on the AgCl layer and the groove in a dry thickness of 30 μm.

Using a paper bridge or a cotton thread, the efficiency of the thus prepared $K^{\oplus}$ ion selective electrode was evaluated by $K^{\oplus}$ activity in the sample liquid through a differential method as in Example 4.

The results are shown in Table 3, in which VERSATOL was employed as a reference liquid.

TABLE 3

| | VERSATOL AA | VERSATOL | VERSATOL AA (+ 6 mmol KCl) |
|---|---|---|---|
| $K^\oplus$ Activity (meq/l) | 3.1 | 4.6 | 9.1 |
| Potential (mV) | −11.2 | −0.1 | 15.2 |

A linear relationship was obtained between logarithm of $K^\oplus$ activity and potential and its potential slope was 58.1 mV.

EXAMPLE 7

A $Na^\oplus$ ion selectrive electrode was obtained in a manner similar to Example 2 except that a sodium ion selective layer having a dry thickness of 25 μm was formed by coating a solution comprising:

| | |
|---|---|
| VYNS | 0.9 g |
| Dioctyl phthalate | 2.4 g |
| MEK | 5 g |
| Methylmonencin | 0.22 g | on a AgCl layer and the scratch-grooved portion.

By a differential method using 140 meq/l of $Na^\oplus$ activity as a reference liquid, a potential slope for $Na^\oplus$ ion of 56 mV was obtained.

EXAMPLE 8

An ion selective electrode was prepared in a manner similar to Example 2 except that a coating solution for an ion selective layer comprising:

| | |
|---|---|
| Polyvinyl chloride | 10 g |
| 4-Octyltrifluoroacetophenone | 5 g |
| Didodecyl phthalate | 10 g |
| Trioctylpropyl ammonium chloride | 0.4 g | was coated to form an ion selective layer for $CO_3^{2\ominus}$.

Evaluation as per Example 7. The results indicate that a linear relationship was obtained between the logarithm of $CO_3^{2\ominus}$ activity and potential and its potential slope was 27 mV.

EXAMPLE 9

An ion selective electrode was obtained in a manner similar to Example 2 except that a chlorine ion selective layer having a dry thickness of 28 μm was formed.

Usisng a cotton thread as a bridge, solutions having $Cl^\ominus$ activities of 77 meq/l and 120 meq/l were measured using VERSATOL (103 meq/l) as a reference liquid.

The results shown in Table 4 were obtained.

TABLE 4

| | 77 meq/l | Reference Liquid 103 meq/l | 120 meq/l |
|---|---|---|---|
| Potential (mV) | 7.0 | −0.1 | −4.1 |

As is clear from Table 4, a good relationship was obtained between the logarithm of $Cl^\ominus$ activity and potential.

EXAMPLE 10

A PET film having a thickness of 180 μm, on which silver having a thickness of 800 nm was deposited, was cut into a size of 32 mm ×200 cm. The edge portions (to be masked from subsequent oxidative-chlorination) of the silver-deposited PET film were masked using a conventional liquid masking agent in a manner similar to Example 1 and oxidative-chlorination was carried out in accordance with Example 1. Then, a 0.2M aqueous KCl solution containing 5% of polyvinyl alcohol was coated on the PET film to provide an electrolyte layer having a dry thickness of 5 μm thereon. Thereafter, scratch-grooving was carried out in accordance with the procedure of Example 1 to render electrical insulation complete. The groove had a width of 80 μm and a depth of 120 μm. Further, a potassium ion selective layer having the composition as described in Example 6 was provided thereon to prepare an electrode having a groove.

The efficiency of the electrode described above was evaluated as in Example 6. Results similar to Example 6 were obtained.

A film-form electrode having a groove for the measurement of $Na^\oplus$, $CO_3^{2\ominus}$ and $Cl^\ominus$ was prepared by repeating the same procedure as described above except that a sodium ion selective layer, a $CO_3^{2\oplus}$ ion selective layer and a chlorine ion selective layer having the compositions shown in Examples 7, 8 and 9 were provided, respectively, in lieu of the potassium ion selective layer described above.

The efficiency of each of the electrodes was evaluated as in Example 6. Similar results were obtained.

EXAMPLE 11

Film-form ion selective electrodes having a scratched groove for $Na^\oplus$, $CO_3^{2\ominus}$ and $Cl^\ominus$ measurements were prepared, respectively, in a manner similar to Example 10 without performing oxidative-chlorination and thereafter ion selective layers having the compositions described in Examples 7, 8 and 9 were directly formed thereon.

The potential slope of each of the electrodes was in a range of from 50 to 60 mV.

EXAMPLE 12

In Examples 1 through 11 described above, a paired electrode was obtained at the same time. A single electrode can be prepared as shown below.

Upon scratch-grooving a silver-deposited PET film formed as in Example 2, two scratched grooves 110A and 110B were formed as shown in FIG. 2. After this scratch-grooving procedure, an ion selective layer 14 (or a protective layer) was provided thereon to cover the entire surface thereof excluding connection terminals 52A and 52B therewith. Then, cutting was effected along line X-X between groove 110A and groove 110B to obtain two single electrodes.

By the use of one single electrode thus obtained as an opposite electrode (which becomes a reference electrode) for $Cl^\ominus$ in combination with another electrode for $K^\ominus$, $Na^\oplus$ or $CO_3^{2\ominus}$ measurement obtained by coating a composition described in Example 6, 7 or 8, respectively, an ionic activity measuring device for direct measurement could be prepared.

EXAMPLE 13

Silver having a thickness of about 500 nm was deposited onto PET film having a thickness of 180 μm and the film was cut into pieces of a size of 32 mm ×2 m. Then, two scratched grooves 110F were formed at intervals of 1 mm in the length direction such that the middle of the two grooves was located at the center of the 32 mm width, each groove having a 100 μm width and a 80 μm depth, as shown in FIGS. 4 through 6. Further grooves (each having a 100 μm width and a 80 μm depth) were formed at intervals of 6 mm in the width direction. Thereafter, a silver portion (52) as shown in FIG. 4 functioning as a terminal was left and oxidative-chlorination was performed as in Example 2.

An ion selective layer having the composition as described in Examples 6 to 9 or a protective layer having the composition as described in Examples 4 and 5 were provided respectively, on the Ag/AgCl electrode. Then, the film was cut off almost at the center between the scratched grooves 110F formed at the 1 mm intervals in the length direction and at the center of each group composed of the three scratched grooves formed at the 6 mm intervals in the width direction. Thus, a single electrode element comprising a paired ion selective electrode for $K^\oplus$, $Na^\oplus$ and $CO_3^{2\ominus}$ measurements in which each of three sides was electrically insulated by a scratched groove was obtained, respectively. The efficiency of each of the paired electrodes was equivalent to that of the electrodes in which only one side was insulated by one groove.

EXAMPLE 14

Figure 11:
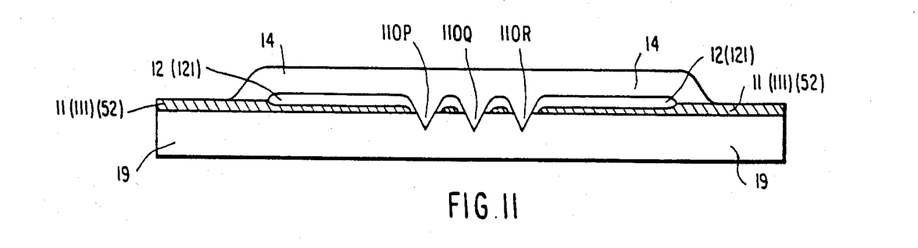

Silver having a thickness of about 500 nm was deposited onto a PET film having a thickness of 180 μm and the film was cut into pieces of 32 mm ×2 m. Then, three scratched grooves 110P, 110Q and 110R (the three grooves constituted one group) were continuously formed at intervals of 1 mm (such that the middle groove was located at the center of the 32 mm width), each groove having a 100 μm width and a 80 μm depth, in the length direction as shown in FIGS. 9 through 11. Further, groove 110S having a 100 μm width and a 80 μm depth was formed at intervals of 6 mm and 1 mm in the width direction. Thereafter, a silver portion (52) as shown in FIG. 9 functioning as a terminal was left and oxidative-chlorination was performed as in Example 2.

An ion selective layer having the composition as described in Examples 6 to 9 or a protective layer having the compositions as described in Examples 4 and 5 were provided, respectively, on the Ag/AgCl electrode. Lastly, the film was cut off almost at the center of the 1 mm interval of groove 110S. Thus, a single electrode element comprising a paired ion selective electrode for $K^\oplus$, $Na^\oplus$ and $CO_3^{2\ominus}$ measurements in which three sides were electrically insulated by the three grooves or the single groove were obtained, respectively. The efficiency of each of the electrodes was equivalent to that of the electrodes in which only one side was insulated by a groove.

While the invention has been described in detail and with reference to specific embodiments thereof, it will be apparent to one skilled in the art that various changes and modifications can be made therein without departing from the spirit and scope thereof.

What is claimed is:

1. In a process for preparing an ion selective electrode which comprises laminating, in sequence, a conductive layer and an ion selective layer on a support, the improvement which comprises forming at least one groove through said conductive layer, which forms at least two electrically separate conductive layers, at least one of which provides an electromotive force, and forming an ion selective layer over said conductive layer such that said groove is filled with said ion selective layer, whereby antishorting is achieved.

2. The process as claimed in claim 1 wherein said groove has a depth to an extent that said support is not divided into two portions.

3. The process as claimed in claim 1 wherein said groove is formed before a layer of a water insoluble salt of the conductive metal employed for said conductive layer is provided on said conductive layer.

4. The process as claimed in claim 3 wherein said conductive layer is a silver layer and said water insoluble metal salt layer is a silver halide layer.

5. The process as claimed in claim 4 wherein said silver halide layer is formed by subjecting said silver layer to oxidative-halogenation.

6. The process as claimed in claim 4 wherein said silver halide layer is a silver chloride layer.

7. The process as claimed in claim 1 wherein said groove is formed after an electrolyte layer is further provided on said water-insoluble metal salt layer.

8. The process as claimed in claim 1 wherein said groove is formed after a water-insoluble metal salt layer is provided on said conductive layer.

9. The process as claimed in claim 1 wherein said groove has a depth of at least 10 times the thickness of said conductive layer.

10. The process as claimed in claim 1 wherein said groove has an opening width of 10 μm to 1 mm.

11. The process as claimed in claim 1 wherein said conductive layer is selected from the group consisting of a layer of a conductive metal and a layer of a conductive metal oxide.

12. The process as claimed in claim 11 wherein a layer of a water-insoluble salt of the conductive metal employed for said conductive layer (a water-insoluble metal salt layer) is provided between said conductive layer and said ion selective layer.

13. The process as claimed in claim 12 wherein said conductive layer is a silver layer and said water-insoluble metal salt layer is a silver halide layer.

14. The process as claimed in claim 13 wherein said silver halide layer is a silver chloride layer.

15. The process as claimed in claim 12 wherein an electrode layer is provided between said water-insoluble metal salt layer and said ion selective layer.

16. The process of claim 1, wherein said ion selective layer covers at least a portion of the surface of the conductive layers on both sides of the groove.

17. The process of claim 16, which comprises in sequence:
providing a conductive layer on the support;
skiving to form the groove, whereby at least two electrically separate conductive layers result, at least one of which provides an electromotive force;
covering the entire surface of the resulting conductive layers and filling the groove with the ion selective layer, whereby anti-shorting is achieved solely due to said ion selective layer.

18. The process of claim 17, which comprises, in sequence:
providing a silver layer on the support to form the conductive layer;
skiving to form the groove, whereby at least two electrically separate silver layers result;
masking at least a part of one of the silver layers, whereby the same will not be oxidatively halogenated and can serve as an electrical terminal;

oxidatively halogenating to form a silver halide layer on the silver layer;

covering the entire surface of the silver halide layer and filling the groove with the ion selective layer, whereby anti-shorting is achieved solely due to said ion selective layer.

19. The process of claim 18, wherein at least five grooves are skived through the silver layer into the support, whereby at least two silver areas completely surrounded by the grooves are formed, all of the grooves being filled with the ion selective layer, whereby the at least two silver layer areas are completely covered with the ion selective layer.

20. The process of claim 19, wherein the silver layer is initially quadralateral in shape, and skiving is conducted inside two of the four edges of said silver layer to form a first pair of grooves which are in parallel and further skiving is conducted in the interior of the conductive layer in a direction perpendicular to said first set of grooves which are in parallel to thereby form at least one second groove which intersects both of said first pair of grooves, all of said grooves being filled with the ion selective layer, whereby a paired ion selective electrode is obtained.

21. The process of claim 20, wherein the at least one second groove comprises at least three grooves.

22. The process of claim 21, wherein the ion selective layer comprises an ion carrier, an ion carrier solvent and an organic hydrophobic binder, and the ion selective layer is formed by coating and drying a solution of the same.

* * * * *